United States Patent
Carucci

[19]

[11] Patent Number: 5,873,724
[45] Date of Patent: Feb. 23, 1999

[54] DENTAL IMPLANTS FOR IDENTIFICATION PURPOSES

[76] Inventor: Carmine A. Carucci, 33 Mount Vernon St., Dover, N.H. 03820

[21] Appl. No.: 59,130

[22] Filed: Apr. 13, 1998

[51] Int. Cl.⁶ ........................................... A61C 3/00
[52] U.S. Cl. ................................. 433/215; 433/229
[58] Field of Search ..................... 433/229, 215, 433/218

[56] References Cited

U.S. PATENT DOCUMENTS

| | | | |
|---|---|---|---|
| Re. 30,594 | 4/1981 | Samis | 433/229 |
| 4,208,795 | 6/1980 | Mühlemann et al. | 433/203 |
| 4,439,154 | 3/1984 | Mayclin | 433/229 |
| 4,512,744 | 4/1985 | Michnick et al. | 433/229 |
| 4,557,693 | 12/1985 | Elggren | 433/229 |
| 4,797,101 | 1/1989 | Morris | 433/229 |
| 4,820,160 | 4/1989 | Cohen et al. | 433/229 |
| 5,037,301 | 8/1991 | Michnick et al. | 433/229 |
| 5,044,955 | 9/1991 | Jagmin | 433/229 |
| 5,509,805 | 4/1996 | Jagmin | 433/229 |

*Primary Examiner*—Cary E. O'Connor
*Attorney, Agent, or Firm*—Thomas J. Engellenner; Lahive & Cockfield, LLP

[57] ABSTRACT

Apparatus and methods for providing personal identifying indicia are disclosed including a protective envelope having a high melting point and substantial corrosion resistance that is dimensioned to fit within a recess formed within a surface of a tooth. Also an identification carrier having identifying indicia placed on it being dimensioned to fit within the protective envelope which is then placed within the protective envelope and bonded within the tooth. The envelope may be constructed from various refractory materials, such as titanium or a zirconium alloys or compounds, in order to provide high temperature and corrosion resistance and the protective envelope can be sealed after the identifying indicia is placed within.

14 Claims, 6 Drawing Sheets

DENTAL IMPLANTS FOR IDENTIFICATION PURPOSES

BACKGROUND OF THE INVENTION

This invention relates to methods and apparatus for identifying people and in particular to methods and apparatus that involve implanting identifying indicia within at least one tooth of a subject.

Identification of the remains of people killed in both man-made and natural disasters has become increasingly scientific over time. Although direct identification of the remains by either a family member or close friend of the deceased is the usual method for identifying deceased individuals, this can be impossible in the case of disasters which are traumatic and destructive in nature. If personal identification is not possible, fingerprints can sometimes be used. Fingerprints, however, suffer from two inherent problems: (1) a fairly small percentage of the overall population have their fingerprints on file; and (2) in the case of a cataclysmic accident, fingerprints may not be available due to the trauma that the body has undergone.

Dental records are often used in disaster cases with a high degree of accuracy. However, there must be some idea as to who the individual might be in order to obtain the dental records. Thus, the use of dental records typically precludes a quick identification of the body. This leaves the friends and family members of the deceased without answers for a long period of time. For example, airline accidents in which a large number of people are killed often have a very traumatic collision and/or a fire burning at high temperatures.

Moreover, with the increasing problem of missing children in today's society, there is a need to identify children, especially after the child has been missing for many years. Photographic evidence in identifying children after several years is of limited efficacy due to the changing nature of a child's appearance as they mature. Although fingerprints are ideal for this use, since they do not change with the passage of time, there has been a general resistance to the fingerprinting of children and also as to where those fingerprint records should be kept.

Therefore what is needed is an apparatus for the identification of a person which does not change or decay with age, which is resistant to severe trauma, to high temperatures, and is resistant to corrosive environments and is easy to insert and remove and read with little discomfort or technology required.

SUMMARY OF THE INVENTION

Apparatus and methods for providing personal identifying indicia are disclosed, including a protective envelope having a high melting point and substantial corrosion resistance that is dimensioned to fit within a recess formed within a surface of a tooth. Also an identification carrier having identifying indicia placed on it being dimensioned to fit within the protective envelope which is then placed within the protective envelope and bonded within the tooth. The envelope may be constructed from various refractory materials, such as titanium or a zirconium alloys or compounds, in order to provide high temperature and corrosion resistance and the protective envelope can be sealed after the identifying indicia is placed within.

The information carrier can include microfiche or gold film on which the identifying information has either been photographically reproduced or engraved, for example, the identifying information can be the social sec The protective envelope after being placed within the recess within the surface of the tooth is then bonded to the tooth and the bonding agent can be colored in order to visually indicate the presence of the identifying apparatus.

Methods for providing, personal identifying indicia are also disclosed. A first method includes the steps of placing identifying indicia on an information carrier, providing a protective envelope, placing the information carrier within the protective envelope, and affixing the protective envelope within the recess of a tooth.

DETAILED DESCRIPTION

Figure 1:
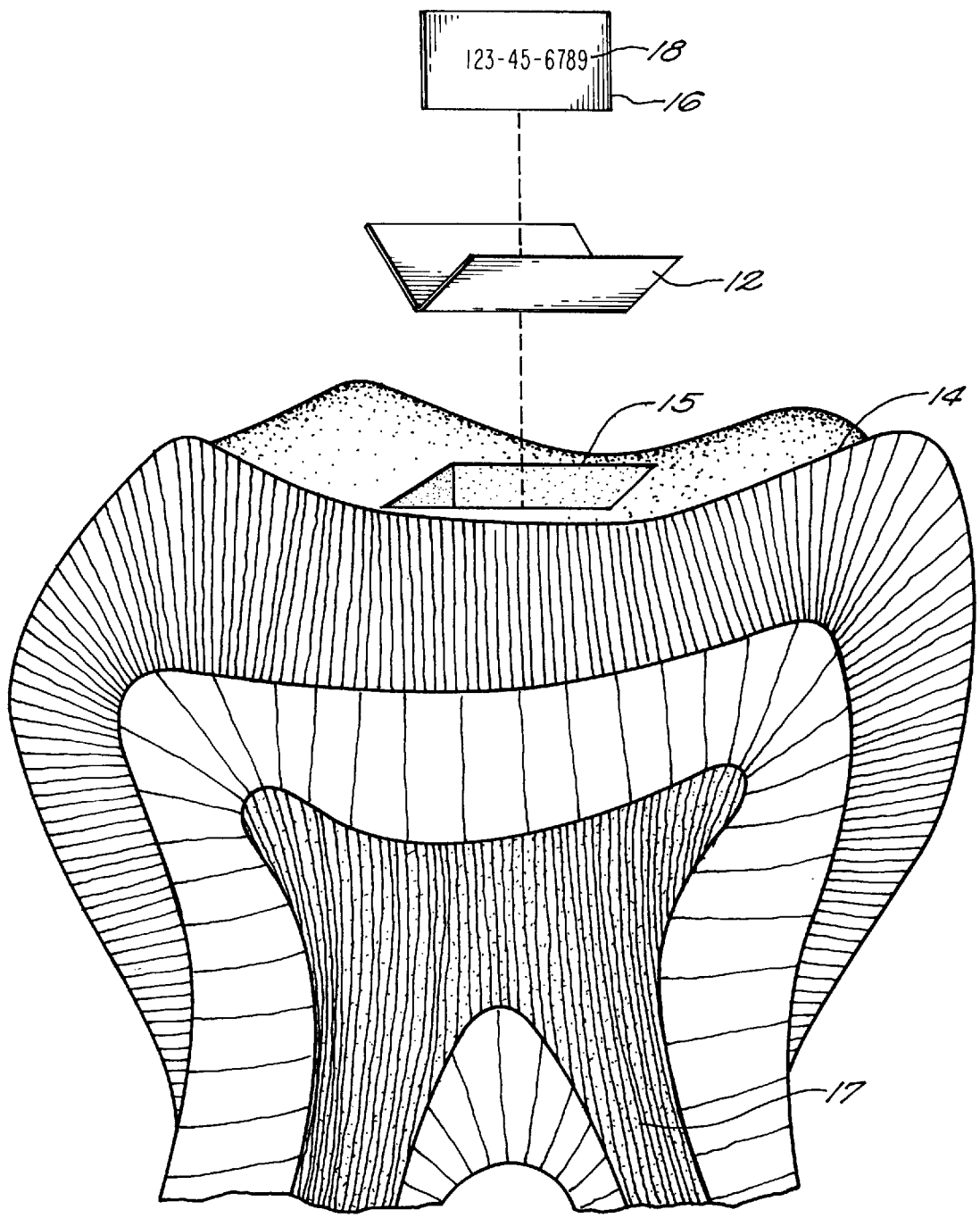
FIG. 1 is exploded view of one embodiment of an apparatus according to the present invention in the form of a dental implants.

An apparatus for providing personal identification adapted for being implanted within a recess of a tooth is shown generally at 10. The apparatus includes a protective envelope 12 being dimensioned to fit within the recess 15 of a tooth 14. An information carrier 16 having identifying indicia 18 is placed within the protective envelope 12, and the protective envelope containing the identifying indicia is then affixed within the recess 15 in a tooth 14.

Figure 2A:
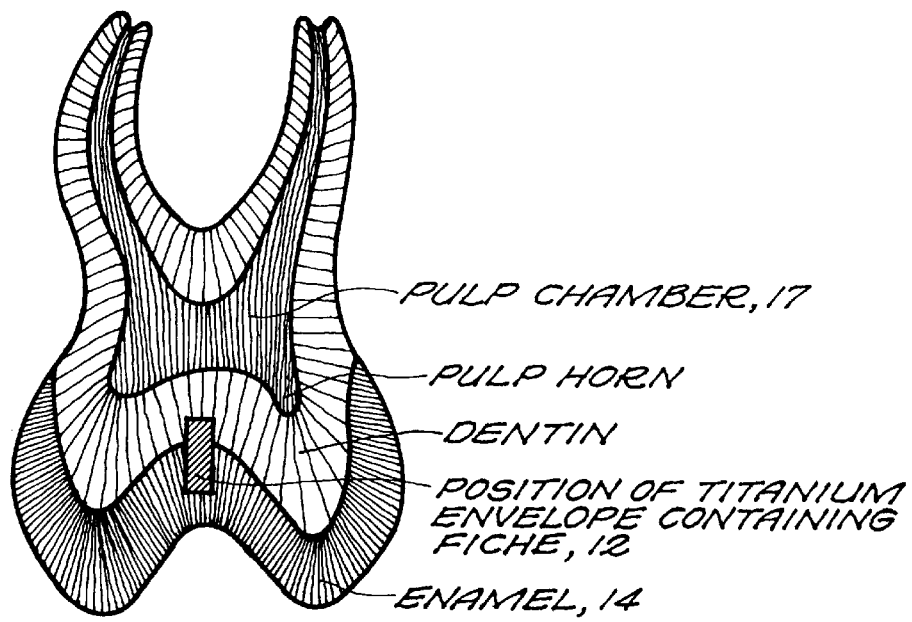
FIG. 2A is a cross-sectional view of a maxillary tooth showing the location of the dental implant of the present invention.

FIG. 2A and 213 show the preferred location to place the protective envelope 12 within the tooth 14. Preferably, the tooth selected can be one of the permanent molars and in particular the maxillary right first permanent molar or the mandibular left first permanent molar are performed. As shown in FIG. 2a the protective envelope 12 is placed in a vertical orientation deep within the tooth for maximum protection. It is of critical importance, however, that the vitality of the tooth is not compromised. Therefore it is critical that the protective envelope 12 be a safe distance from the vital pulp tissue 17.

Figure 2B:
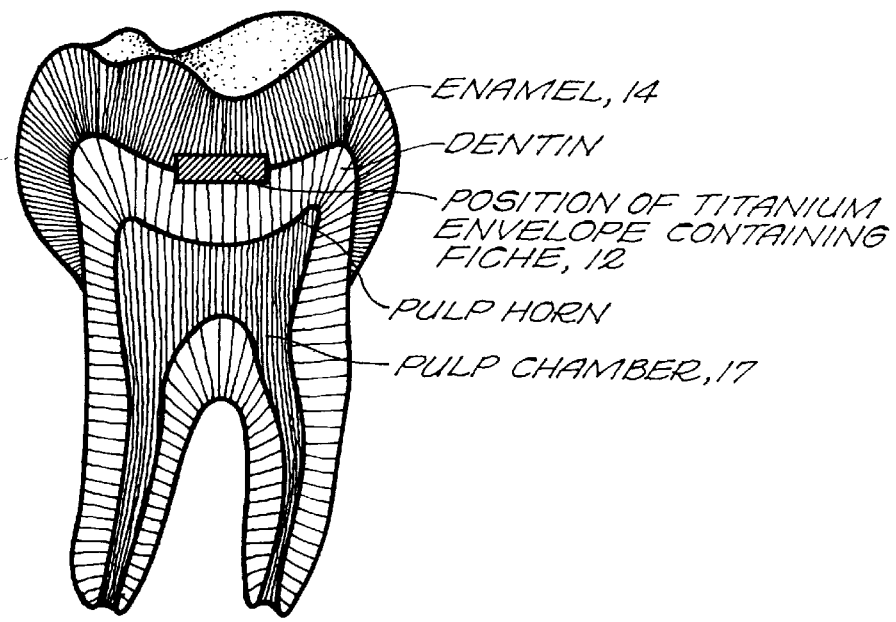
FIG. 2B is a cross-section of a deciduous mandibular molar tooth showing the location of the dental implant.

Although a permanent tooth is preferred, FIG. 2B discloses the position of the protective envelope 12 within a deciduous tooth, usually the maxillary or mandibular first molar. Due to the smaller size of the deciduous teeth the protective envelope is placed in a horizontal position and in a shallower recess 15 within a tooth 14. The useful life of the identifying information will, of course, be much lower due to the exfoliation of the tooth during the normal growth process.

Figure 3:
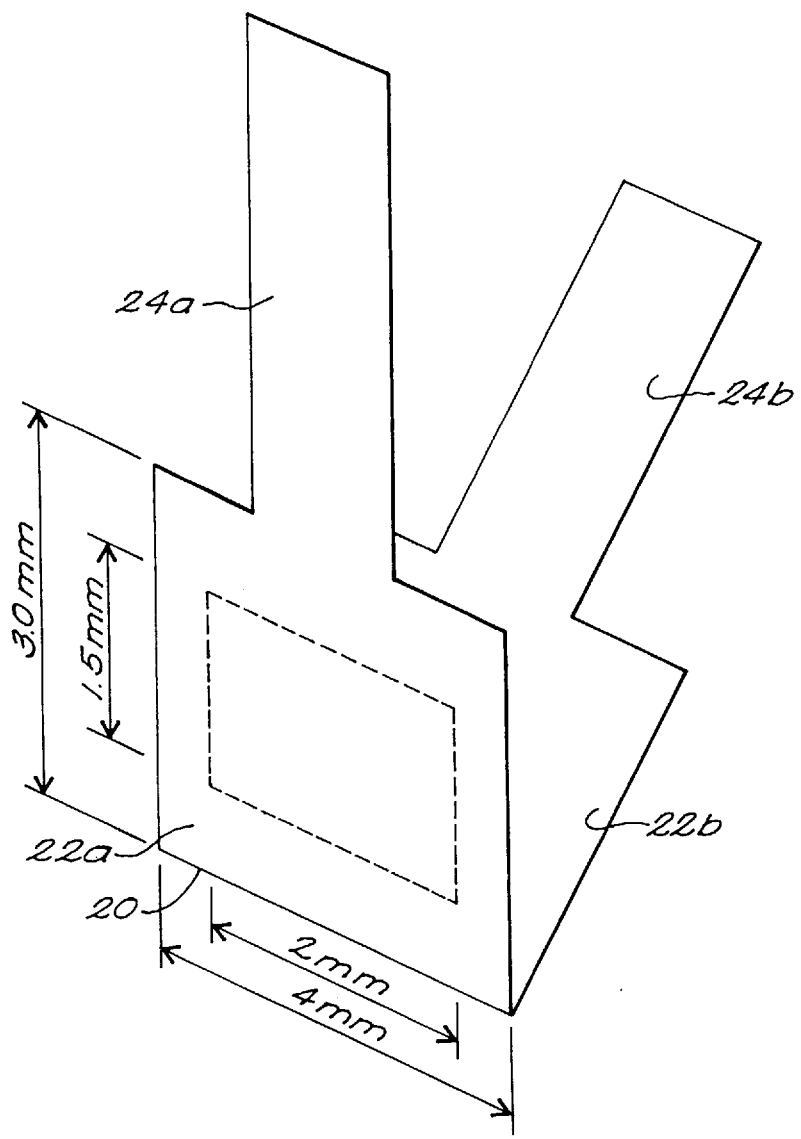
FIG. 3 is a plan view of the preferred embodiment of the protective envelope of the present invention.

FIG. 3 shows a plan view of the protective envelope 12 showing the preferred embodiment. The protective envelope 12 preferably comprises a hinged portion 20 and two side portions 22a and 22b. The side portions 22a and 22b preferably each have a tab 24a and 24b attached to the end opposite from the hinged portion 20. In the preferred embodiment the two side portions 22a and 22b are 3.0 mm×4.0 mm, and the tab portions extend 4.0 mm, and are wide enough to be easily grasped by forceps.

In order to withstand the extreme temperatures and extremely corrosive environment which are involved within the spectrum of both man-made and natural catastrophes, the protective envelope must be able to withstand extremely high temperatures without melting and provide corrosion resistance in corrosive environments. Preferably the protective envelope is constructed from titanium or a titanium alloy. The titanium alloys, which include alpha-titanium alloy, beta-titanium alloy, alpha-beta-titanium alloys all have certain mechanical properties in terms of the ductility and ability to be welded, and different physical properties in terms of melting point and corrosion resistance. In addition, zirconium and zirconium alloys will also provide a high temperature resistance and corrosion resistance although not to the same level as titanium. In addition titanium has other unique properties which make it a preferred material. Titanium and its alloys are biocompatible and a medical grade of titanium exists. In addition, titanium is not magnetic, and its surface ionization potential is lower than either gold or silver. Titanium has a density less than steel, while having low thermal conductivity, and excellent strength retention at high temperatures.

The information carrier 16 may be any material on which the identifying indicia 18 may be placed upon. For example, photographic methods may be used for imprinting the identifying indicia 18 on the surface of the information carrier. The information carrier may be photographically placed on a piece of film, i.e. microfiche, or microfilm, or the identifying indicia may be printed on a material suitable for placement within the protective envelope 12. Alternatively, a material such as gold film may be used which allows the identifying indicia to be engraved or embossed with the identifying indicia and then placed within the protective envelope 12. Gold film being malleable yet corrosion resistant would be preferred. In one preferred embodiment of the present invention, microfiche is used to record the identifying indicia 18. As would be obvious to one of skill in the art, the number of materials available on which information may be placed for retrieval at a later time is extremely large, and it would be an obvious design choice to substitute for one of these other materials as the information carrier 16.

Figure 4:
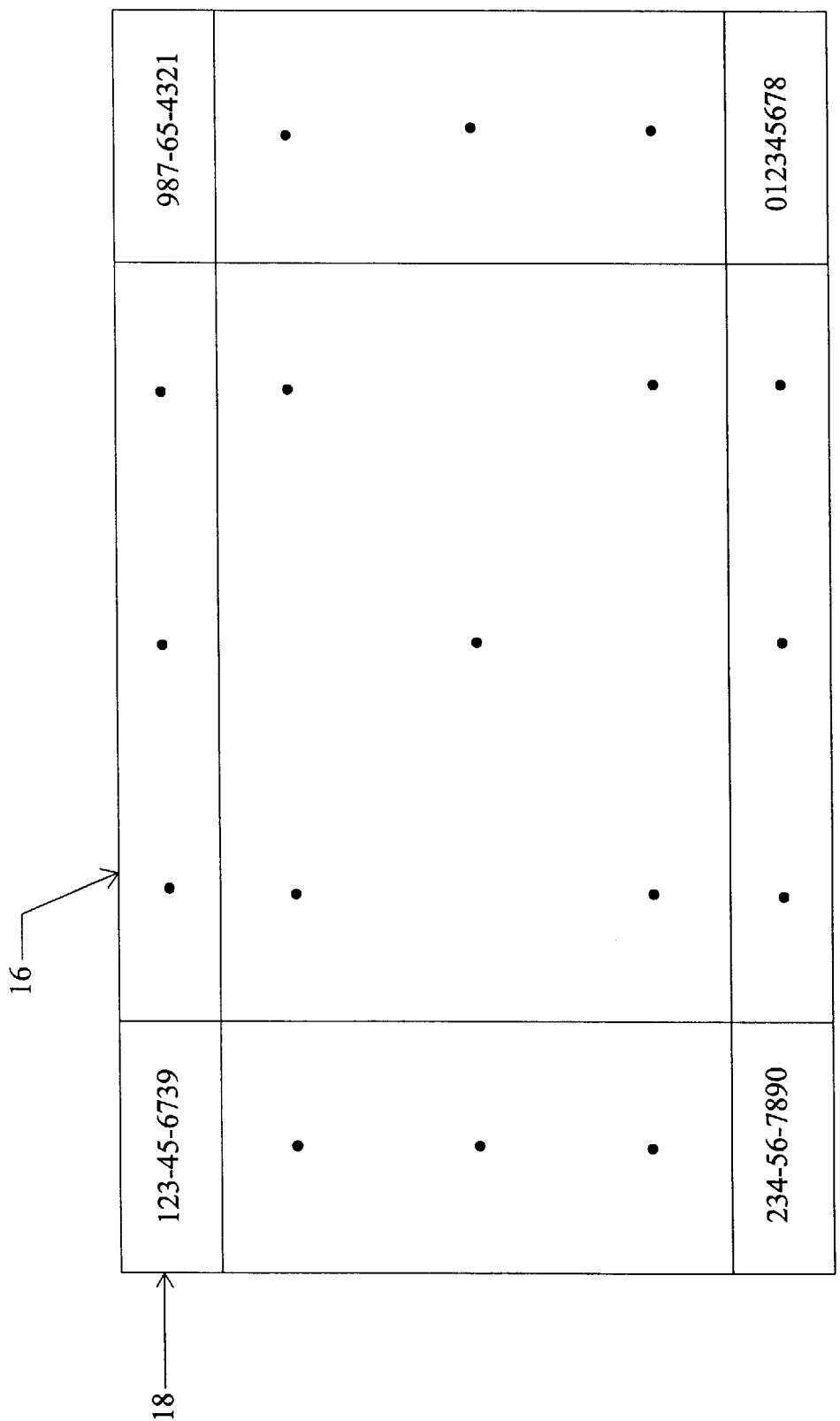
FIG. 4 is a plan view of a piece of photographic acetate showing the orientation of information carriers and identifying information induce thereon.

FIG. 4 shows the preferred embodiment of the formation of individual information carriers 16 on a single piece of photographic acetate 26. Preferably the information carrier 16 is a sheet of photographic microfiche acetate 26, which can be processed by various commercial facilities. The identifying indicia 18 is provided to the laboratory and is placed on photographic microfiche acetate. Each piece of photographic microfiche acetate 26 is approximately 3.5"× 5.5" and is able to hold identifying indicia 18 in 208 individual information carriers 16. Each individual information carrier 16 is 2.0 mm×1.5 mm. The size of each individual information carrier 16 is sized to provide a buffer of acetate material around the identifying information for safe handling. Each individual information carrier 16 may be individually separated from the photographic acetate with a sharp knife.

The identifying indicia 18 may be any piece of information capable of uniquely identifying the individual. It would be obvious to one of skill in the art that a person's name or social security number may be used, or a number specific to the identification system may be used. In preferred embodiment, the person's society security number or military I.D. number is used.

The identifying indicia may be placed in the information carrier in many ways. It would be obvious to one of skill in the art that the numbers or letters may be written or encoded in a bar-code or other easy to read coding means. Preferably, the social security number is placed as a number on the information carrier. The social security number can be placed below the mid-horizontal line equidistant from the vertical borders of the microfiche. The use of the microfiche and placement of the identifying information on it allows the use of a slide projector to easily view the identifying information. In this way no special technology is required to read the information.

After placing the identifying indicia 18 on the information carrier 16, the personal data of the individual identified by the identifying indicia 18 is stored in a data storage system. It would be obvious to one of skill in the art, that the data storage system may be as simple as an index card filing system or as complex as an electronic database stored within a computer's memory. In one preferred embodiment the data is stored within a computer memory and is accessed by a suitable computer program.

Figure 5:
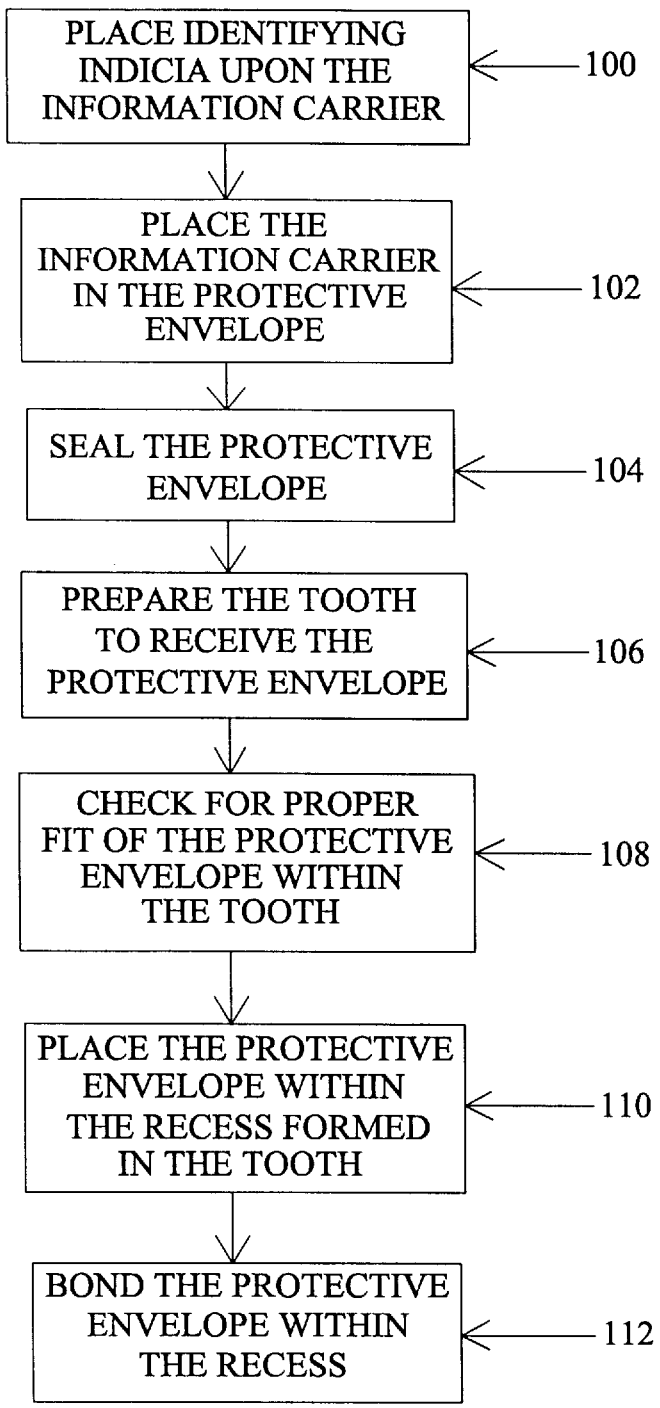
FIG. 5 is a flow chart of the method of inserting the dental implant for identification purposes into a tooth.

A method is disclosed in FIG. 5 for implanting the identifying indicia within a tooth. In Step 100 the identifying indicia is placed upon the information carrier. The information carrier is then placed within the protective envelope, Step 102, and the protective envelope is sealed enclosing the information carrier in Step 104. The sealing of the protective envelope in Step 104 is preferably accomplished through spot welding the protective envelope. A suitable spot welder is manufactured by the Rocky Mountain Orthodontic Manufacturing Company, Denver, Colo.

The tooth is then prepared to receive the protective envelope in Step 106. As described above, it is extremely critical that the vital pulp tissue within the tooth is not disturbed in order to insure the vitality of the tooth. Therefore preferably an air abrasive instrument is used instead of a conventional rotary drill. The air abrasive instrument makes possible a more conservative preparation thereby saving valuable tooth material. In addition, the air abrasive instrument is usually pain free, very fast, quiet, vibration free and does not require changing drill bits. The air abrasive instrument is used to prepare a class 1 cavity preparation.

The protective envelope is then used to see if the recessed form within the tooth is of the proper depth and size, Step 108. The protective envelope is placed vertically in the cavity preparation with the tabs projecting out of the preparation. The bottom edge of the envelope should be on the floor of the cavity preparation, and the occlusal edge of the envelope should sit low enough in the cavity preparation to allow sufficient clearance for approximately 0.5 mm thickness of bonding cement in the finished product. The sides of the envelope should have enough clearance within the recess to allow free passage of a sickle shaped dental explorer continuously around the periphery of the protective envelope.

The protective envelope is then placed within the recess formed in the tooth, Step 110. The cavity preparation having been checked to insure proper fit when the protective envelope is inserted is first sterilized using any acceptable product and procedure, as would be known to one of ordinary skill in the art. The interior of the preparation is then acid-etched with 37% phosphoric acid for thirty seconds. This followed by a thorough rinsing with water for thirty seconds. Next a very thin coating of a mix of light activated Compomer®, available from Den-Mat Corp. is applied to the cavity preparation. The protective envelope is held firmly on the floor of the cavity preparation using the vertical tabs to push down and the interior of the cavity preparation is then exposed to ultraviolet light which cures the light activated Compomer®. A suitable ultraviolet curing light is available from the Demitron Corporation. Next, the vertical tabs are removed using any suitable pair of scissors.

Next, the remainder of the cavity preparation is filled with Compomer® in order to bond the protective envelope within the recess, Step 112. The Compomer® is then exposed to the UV curing light for approximately twenty seconds. The bonding material is then trimmed and polished in a conventional manner.

Figure 6:
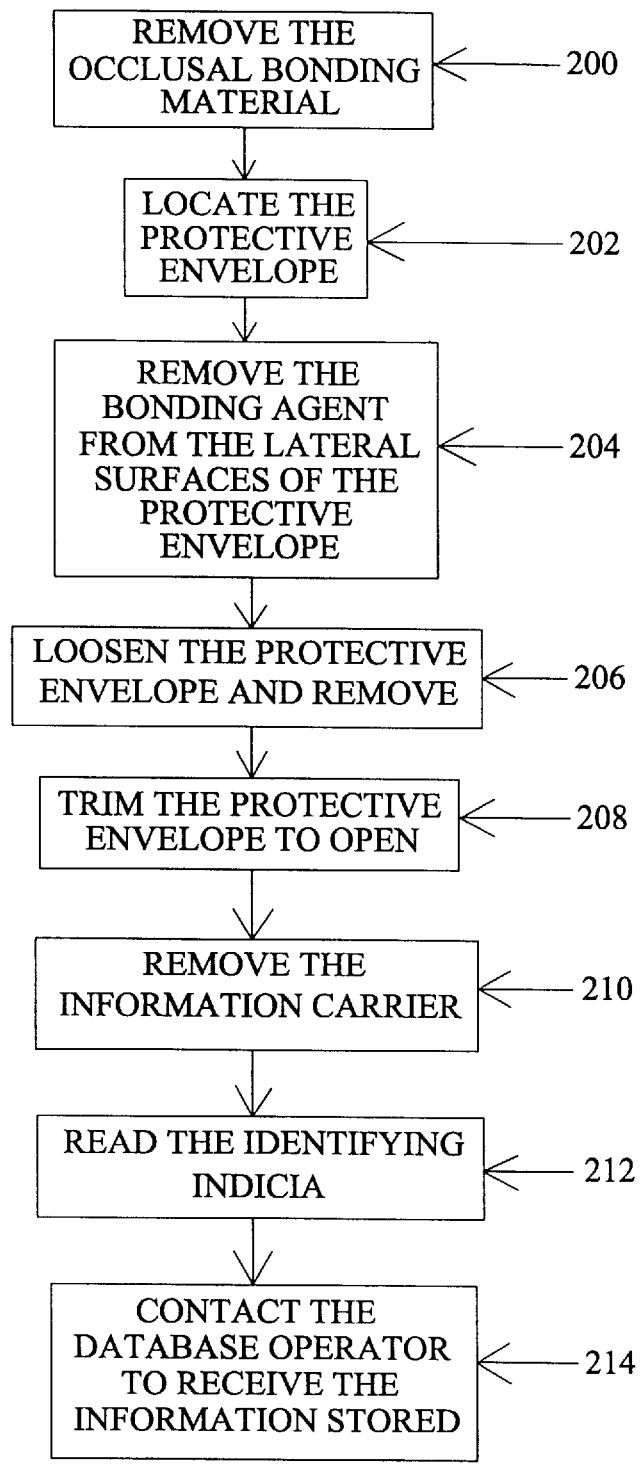
FIG. 6 is flow chart showing the method for retrieval of implanted information and subject to identification thereof.

FIG. 6 discloses a method for retrieval of the implanted information and subject identification. First, the occlusal bonding material is removed, as in Step 200, using an air abrasive instrument or suitable round burr so that the protective envelope may be located, Step 202. Next, using an air abrasive instrument or suitable narrow tapered fissure burr, the bonding agent is removed from between the lateral surfaces of the protective envelope and the cavity wall as in Step 204. Next, in Step 206, the protective envelope is loosened and the protective envelope removed from within the recess of the tooth. When the protective envelope is loosened a thin bladed steel plastic instrument is used. The instrument is placed into the prepared lateral trough and is gently rotated, thus removing more lateral bonding material. This procedure is continued until the protective envelope is loose and able to be retrieved. It is critical not to use excessive force while loosening and removing the protective envelope to avoid fracturing any part of the natural tooth that contains the identifying indicia. If needed, any repair or replacement of the bonding filling to restore tooth function may be done by any standard dental procedure. In step 208, the titanium envelope is removed from the tooth and the protective envelope is trimmed about its periphery in order to open the protective envelope. In Step 210, the information carrier is removed from the protective envelope. It is important that the information carrier be treated gently so as to avoid any scratching of the surface which may mark or obstruct the identifying indicia contained thereon. Preferably the information carrier is removed and handled using a cotton pliers and only handled in the buffer area surrounding the identifying indicia. In step 212 the identifying indicia is read from the information carrier, and a database operator is contacted in order to receive the information stored concerning the person thereof. In one preferred method where the information carrier is microfiche, the microfiche can be read by a conventional slide protector. This enlarges the identifying indicia, which in a preferred embodiment is the person's social security number, allowing the information to be read easily.

What is claimed is:

1. An apparatus for personal identification suitable for being implanted within a recess of a tooth comprising:

a protective envelope dimensioned to fit within a recess formed within a surface of the tooth, the protective envelope having a substantial corrosion resistance, and a high melting point, and an information carrier having identifying indicia being dimensioned to fit within the protective envelope, whereby the information carrier, can be placed inside the protective envelope, and the protective envelope affixed within the recess of the tooth, to protect the information carrier from extreme temperatures and corrosion.

2. The apparatus as in claim 1 wherein the protective envelope is constructed from the among the group of titanium, α titanium alloys, β titanium alloys, α-β titanium alloys, zirconium, and zirconium alloys.

3. The apparatus of claim 1 wherein the information carrier comprises microfiche.

4. The apparatus of claim 1 wherein the information carrier comprises gold.

5. The apparatus of claim 1 wherein the protective envelope is welded shut along the edges, for sealing the information carrier within the protective envelope.

6. The apparatus of claim 1 wherein the protective envelope is welded shut along the edges, for sealing the information carrier within the protective envelope.

7. An apparatus for personal identification suitable for being implanted within a recess of a tooth comprising:

a protective envelope having a closed end and an open end, the protective envelope dimensioned to fit within the recess of a tooth, the protective envelope having a tab extending from at least one edge of the open end for allowing easier handling of the protective envelope during use, the protective envelope having substantial corrosion resistance, and a high melting point, an information carrier having identifying indicia imprinted upon it, the information carrier being sized and dimensioned to fit within the protective envelope, and the information carrier, being placed inside the protective envelope, and the protective envelope being affixed within the recess formed in the surface of the tooth, whereby the information carrier is protected from extreme temperatures and corrosion by the protective envelope.

8. The apparatus as in claim 7 wherein the protective envelope is constructed from the among the group of; titanium, α titanium alloys, β titanium alloys, α-β titanium alloys, zirconium, and zirconium alloys.

9. The apparatus of claim 7 wherein the information carrier comprises microfiche.

10. The apparatus of claim 7 wherein the information carrier comprises gold.

11. A method of placing personal identification in a recess of a tooth comprising the steps of:

placing identifying indicia on an information carrier, providing a protective envelope, placing the information carrier within the protective envelope, and affixing the protective envelope within the recess of the tooth.

12. The method as in claim 11 further comprising the step of sealing the protective envelope.

13. The method as in claim 11 wherein sealing the protective envelope comprises welding.

14. A method of personal identification as in claim 11 further comprising the steps of:

upon the arising of a need to identify an individual, removing the protective envelope from the recess of the tooth, removing the information carrier from the protective envelope, reading the identifying indicia from the information carrier, and interpreting the identifying indicia to identify the individual.

* * * * *